United States Patent [19]
Longo, Jr. et al.

[11] Patent Number: 6,004,539
[45] Date of Patent: Dec. 21, 1999

[54] ANTIMICROBIAL POLISHING COMPOUND

[76] Inventors: James Joseph Longo, Jr., 104 Nevada Ave.; James Joseph Longo, Sr., 1101 Lakewood Dr., both of Wilmington, Del. 19803; David Michael Longo, 1201 W. 9th St., Wilmington, Del. 19806

[21] Appl. No.: 09/250,903

[22] Filed: Feb. 16, 1999

Related U.S. Application Data

[63] Continuation-in-part of application No. 08/932,983, Sep. 18, 1997, abandoned.

[51] Int. Cl.$^6$ ................... A61K 7/16; A61K 7/30
[52] U.S. Cl. ................ 424/49; 424/53; 424/401; 510/116
[58] Field of Search ................ 424/49, 52, 53, 424/55, 401; 510/116, 395, 396, 397; 514/937; 106/3

[56] References Cited

U.S. PATENT DOCUMENTS

| | | | |
|---|---|---|---|
| 3,839,213 | 10/1974 | Hill | 510/116 |
| 4,066,566 | 1/1978 | Lauster | 134/28 |
| 4,561,993 | 12/1985 | Choy et al. | 510/397 |
| 4,701,223 | 10/1987 | Eoga | 134/2 |
| 4,806,173 | 2/1989 | Toukan | 134/42 |
| 4,807,649 | 2/1989 | Eoga | 134/2 |
| 5,026,539 | 6/1991 | Jackson et al. | 424/49 |
| 5,087,444 | 2/1992 | Jackson et al. | 424/49 |
| 5,112,600 | 5/1992 | Jackson et al. | 424/55 |
| 5,624,906 | 4/1997 | Vermeer | 514/23 |

*Primary Examiner*—Robert H. Harrison
*Attorney, Agent, or Firm*—Huntley & Associates

[57] ABSTRACT

An antimicrobial, abrasive, polishing compound, colloidal suspension or gel formulated for the controlling of microbial cross-contamination in the pumicing or polishing of prosthetic and orthodontic dental appliances and related materials. The colloidal suspension provides continuous, instant access to a pre-mixed polishing compound with excellent antimicrobial activity for use by dental offices and laboratories.

21 Claims, No Drawings

ANTIMICROBIAL POLISHING COMPOUND

CROSS-REFERENCE TO RELATED APPLICATION

This is a Continuation-in-Part of U.S. application Ser. No. 08/932,983 Sep. 18, 1997, now abandoned.

BACKGROUND OF THE INVENTION

The present invention relates to compounds for grinding and polishing, such as those used in the dental industry.

Pumice (crushed volcanic rock) is widely used by dentists and dental technicians to abrade, grind, smooth, buff and finish dental acrylics, gold, metals, chrome-cobalt alloys and porcelain and other materials associated with prosthetic and orthodontic dental appliances. In these applications, pumice has generally been used by adding pumice powder to a shallow pan which lies underneath an arbor and polishing wheel of a lathe. Water is then added to the pumice and mixed together to form a polishing medium with the consistency of very fine, wet beach sand. The operator activates the lathe, thus spinning the polishing wheel, and scoops this wet pumice from the pan by hand and applies it to either the polishing wheel, the area of the prosthetic appliance to be polished, or both. The dental appliance is then forced onto the underside of the wheel, while applying an appropriate amount of pressure, to remove deep gouges and rough surfaces created by dental rotary instruments in the fabrication and/or adjustment of the appliance. The amount of time necessary to bring the acrylic surface to one of relative smoothness depends mainly on how abraded the surface is, the volume of area to be polished and the grit size of the pumice used.

Pumice is generally supplied as a crushed powder in which an aqueous liquid, mainly water, is added to wet the powder in order to produce a usable mixture. This wet pumice mixture is generally contained with in a shallow rectangular pan, encased in a splash hood, which lies below a polishing wheel fixed to an arbor connected to a polishing lathe. This wet pumice is then applied to a prosthetic or orthodontic dental appliance or to the revolving wheel of the lathe, and the appliance forced against the wheel to reduce the abraded surfaces of the appliance created mainly by dental rotary instruments during the fabricating and/or adjusting of the appliance. This abrasion of the appliance surface, by the rotary instruments as well as the pumice granules potentially releases microorganisms present on or below the surface of the appliance. This contamination is transferred into the bulk pumice supply below the wheel as well as becomes imbedded in the fibers of the polishing wheel. This microbial contamination can potentially be transmitted to all future appliance cases, the operator and possibly even the patient, presenting a cross-contamination hazard that needs to be rectified.

Throughout the dental community, recommendations have been put forth to enable dentists and laboratories combat this contamination in the pumicing/polishing areas. Generally a mixture of the pumice powder, an Environmental Protection Agency (EPA) approved disinfectant liquid and water are combined to try to control contamination. However, efficacy data for controllability of microbial contamination by this means is not available. Also, many of these disinfectants are extremely corrosive to the skin and eyes, thus proving hazardous for a polishing material that splatters greatly when applied to a high speed polishing wheel of a lathe. Another problem associated with the incorporation of these liquid disinfectants into the pumice powder is the settling of the pumice powder to the bottom of the pan, in which it is held, resulting from gravitational forces. This results in a separation of germicidal liquid and pumice, promoting increased evaporation of the said liquid, thus reducing the amounts of germicidal volume for treating the contamination. Thus, there is no ability to accurately assure the parts per million (ppm) available germicide in the pumice, disinfectant and water mixture are at germicidal levels at the time of polishing an appliance case. Furthermore, the additions of organic materials from ongoing pumicing/polishing of appliance cases, such as tartar, calculus, saliva, blood, mucous and other proteinaceous soils depletes the availability of active germicide, thus depleting the activity level of the germicidal pumice mixture. A further problem associated with the current techniques for pumicing of cases is the lack of efficiency in the continual weighing, diluting, mixing, and adding of the liquids to the pumice powder prior to pumicing steps.

Clinical studies have shown the existence of microbial contamination in the used pumice medium of dental offices and laboratories to be in excess of a quarter billion cells per gram of pumice: a threatening level for a reservoir of potentially pathogenic organisms.

In short, pumice compositions and pumicing techniques, as currently used in the industry, have many disadvantages which prevent the operator from adhering or complying to current guidelines, recommendations and regulations in the dental community. One major disadvantage of the current compositions and techniques is the inability to effectively control the spread of microbial cross-contamination in the pumicing area. Pumice is generally reused from case to case, transferring germs from one dental prosthesis to another and potentially to the operator and possibly even the patient as well. Another disadvantage is the lack of efficiency in preparing the pumice mixture for performing the current techniques. The current techniques of premixing the pumice and liquid and the cleaning and discarding of used material lend themselves to be cumbersome, inefficient, time consuming and messy as well as a potential biohazard for the operator.

SUMMARY OF THE INVENTION

The present invention provides a composition which permits controlling of microbial cross-contamination in the pumice/polishing production areas of the dental office and dental laboratory.

Specifically, the present invention provides an antimicrobial polishing compound consisting essentially of a colloidal suspension of at least about 45% by weight of each of (a) a liquid phase comprising, by weight of the liquid phase about from 90 to 99% water; about from 0.5 to 10% hygroscopic solvent; about from 0.5 to 4% deflocculation agent; and up to about 0. 1% each of preservative and chelating agent; and (b) a solid phase comprising, by weight of the liquid phase about from 70 to 90% abrasive; about from 10 to 20% colloidal suspension agent; and about from 0.5 to 2.5% of at least one antimicrobial agent.

DETAILED DESCRIPTION OF THE INVENTION

The antimicrobial polishing compounds of the present invention consist essentially of a colloidal suspension of at least about 45% by weight of each of a liquid phase and a solid phase. Within this range, the resulting polishing compound exhibits a high viscosity and sticky properties which permit good adhesion to a dental appliance as well as a polishing wheel. Preferably, the liquid and solid phases each comprise at least about 48%, and about 50% of each phase is particularly preferred.

The liquid phase comprises about from 90 to 99% water. Less than about 90% water typically does not provide a polishing compound having sufficient fluidity for conventional dental applications. Distilled water is preferred.

The liquid phase further comprises about from 0.5 to 10% hygroscopic solvent. About from 3 to 6% of this component is preferred, and about 4% has been found to be particularly satisfactory. This component acts as a humectant, and is preferably a plasticizer for the other components in the composition. A wide variety of hygroscopic solvents can be used, including, for example, propylene glycol, glycerine, sorbitol, mono-, di- and triethanol amines, and polyethylene glycol, as well as nonionic and amphoteric surfactants. Of these, propylene glycol has been found to be particularly satisfactory, and is accordingly preferred.

The liquid phase further comprises about from 0.5 to 4% deflocculation agent, to raise the pH of the liquid phase to aid in the dispersion with the solid components. In general, the pH of the liquid phase is adjusted to about from 9.0 to 11.0. Preferably, the defloculation agent is present in an amount of about 2% of the liquid phase. A variety of deflocculation agents can be used, including, for example, sodium silicate, sodium metasilicate, and sodium silicate solutions, generally known as water glass.

The liquid phase can further comprise up to about 0.1% each of preservative and chelating agent.

A wide variety of known preservatives can be used which are bactericidal or bacteriostatic, including, for example, Dimethylol Dimethyl Hydantoin, sodium benzoate, methyl paraben and propyl paraben, and mixtures of one or more of such preservatives. About from 0.05 to 0.1% preservative is preferred, and cis-1-(3-chloroallyl)-3,5,7-triaza-1-azoniaadamantane chloride has been found to be particularly effective in the present compositions.

Chelating agent is preferably present in an amount of about from 0.05 to 0.1% of the liquid phase. The chelating agent is present to bond free metal ions, such as those of magnesium and calcium, that may be in the composition and would otherwise depreciate the performance characteristics of the final product. Specific chelating agents used can be selected, for example, from tri-, di- and tetra-sodium salts of ethylenediaminetetraacetic acid (EDTA), calcium salts of EDTA,. and sodium gluconate. Of these, the tetra-sodium salt of EDTA is preferred. Still other chelating agents will be evident to those skilled in the art.

The solid phase comprises about from 70 to 90% abrasive. Abrasives which can be used include, for example, pumice, aluminum oxide, aluminum silicates, calcium carbonate, diamond, flint pebbles, silicon dioxide, silicon carbide, zirconium oxide and crushed nut shells such as walnut. Pumice is particularly preferred. The pumice or other abrasive which is used can be of various grits corresponding to specific micron sizes spanning approximately fifteen (15) to eight hundred (800) microns.

The solid phase further comprises about from 10 to 20% colloidal suspension agent, and preferably about from 14 to 18% of the solid phase. Colloidal suspension agents which can be used include Bentonite, other aluminum silicates and colloidal clays such as kaolin, diatomaceous earth and fullers earth; colloidal silica; natural polymers such as starches, gelatins, phycocolloids; semi-synthetic cellulose derivatives such as carboxy-methyl-cellulose (CMC); and synthetic colloidal agents such as polyvinyl alcohol, and carboxy-vinylates.

A central component of the present antimicrobial compositions is at least one antimicrobial agent. The antimicrobial agent should be present in an amount of about from 0.5 to 2.5% of the solid phase. Known antimicrobial agents which can be used include 2,4,4-trichloro-2-hydroxydiphenyl ether, commercially available as "Triclosan" or "Irgasan DP 300" from Ciba-Geigy Corporation; and 3,4,4"-trichlorocarbanilide, N-(4-Chlorophenyl-N-3,4-dichlorophenyl) Urea, commercially available from Nipa Hardwicke Incorporated as "Triclocarban" or "Nipaguard TCC." Still other antimicrobial agents which can be used in the present invention include quaternary ammonia compounds such a benzalkonium chloride; bisbiguanides such as chlorhexidine; phenolic compounds and derivatives such as p-chloro-m-xylenol (PCMX), halogenated compounds and their derivatives such as iodophors, hypochlorites and Chloamine T and B.

In the preparation of the polishing compounds of the present invention, the liquid phase and the solid phase are first separately prepared, each admixed to provide a substantially homogenous blend of the components. The liquid phase and the solid phase are then combined in a mixing apparatus, such as a planetary action paddle mixer, to provide the final polishing compound.

The resulting polishing compound can be packaged, using conventional techniques, in an aseptic delivery concept such as a squeezable, toothpaste-type, dispensing tube. In this way, the used compound never comes into contact with the unused compound, thus preventing possible cross-contamination. Similarly, the polishing compound can be packaged in a single use, disposable container. It also affords the operator quick easy access to an antimicrobial pumicing medium without the hassles associated with the weighing, diluting, mixing, and adding of liquids to pumice to generate a pumicing medium. The invention thus provides a proven, pre-mixed, antimicrobial biocidal, pumicing compound for use in the fabricating and adjusting of prosthetic and/or orthodontic appliances. Moreover, the polishing compounds of the present invention exhibit long term excellent stability, in that the abrasive does not separate from the antimicrobial component over a period of at least two (2) years. The antimicrobial properties are similarly stable over a two (2) year period.

While there has been described preferred compositions and embodiments of the antimicrobial polishing compound of this invention, it is understood that changes in chemical composition, chemical ingredient ratio, pH, materials, sizes, weights and packaging or containment configurations can be made by those skilled in the art without departing from the invention.

The present invention is illustrated by the following specific Examples.

EXAMPLE 1

A polishing compound was prepared by first separately admixing the components of a liquid phase and a solid phase and then combining the two phases, all according to the following procedures:

Liquid phase: 100.00 grams

1. Weigh out and add to a clean beaker, 93.850 grams of water (preferably distilled).

2. Weigh out separately, 2.000 grams of sodium silicate solution (N) and add to the water with continuous mixing.

3. Weigh out separately, 4.000 grams of propylene glycol and add to the above mixture while continuously mixing.

4. Weigh out separately, 0.075 grams of Dowicil® 200 and add to the above mixture while continuously mixing.

5. Weigh out separately, 0.075 grams of tetrasodium EDTA and add to the above mixture while continuously mixing.

6. Thoroughly mix the above solution for fifteen minutes and let stand.

Solid phase: 100.00 grams

1. Weigh out and add to a clean mixing bowl, 80,860 grams of pumice.

2. Weigh out separately, 16.005 grams of bentonite and add to the above pumice. Thoroughly blend together with a beater type blending apparatus until a uniform distribution of the two is obtained.

3. Weigh out separately, 2.090 grams of Triclosan and add to above mixture and repeat blending with beater until a uniform distribution is obtained.

4. Weigh out separately, 1.045 grams of Triclocarban and add to above mixture and repeat blending with beater until a uniform distribution is obtained.

5. Blend mixture an additional ten minutes and let stand.

Compound formulation: 180.00 grams 52.00% liquid phase/48.00% powder phase.

1. Weigh out and add to a clean mixing bowl, 86.40 grams of the above powder phase.

2. Weigh out and add to a clean beaker, 93.60 grams of the above liquid phase.

3. Place the mixing bowl containing the 86.40 grams of the powder phase under the beater and with continuous mixing in a planetary type motion, slowly add the pre-weighed 93.60 grams of the liquid phase until exhausted.

4. Blend the above mixture continuously until a uniform colloidal suspension is obtained, being careful to blend away any flocculation during the mixing process.

The formula breakdown for the preferred liquid phase of the said antimicrobial pumicing compound is:

| Ingredient: | Percentage: |
| --- | --- |
| 1. Water | 93.85% |
| 2. Propylene Glycol | 4.00% |
| 3. Sodium Silicate Solution (N) | 2.00% |
| 4. Dowicil® 200 | 0.075% |
| 5. Tetrasodium EDTA | 0.075% |
| TOTALS: | 100.00% |

The formula breakdown for the preferred powder phase of the said antimicrobial pumicing compound is:

| Ingredient: | Percentage: |
| --- | --- |
| 1. Pumice | 80.960% |
| 2. Bentonite | 16.005% |
| 3. Triclosan | 2.090% |
| 4. Triclocarban | 1.045% |
| TOTALS: | 100.00% |

The formula breakdown for the preferred combination of liquid ingredients to powder ingredients in order to form the antimicrobial compound is: 52.00% Liquid Ingredients to 48.00% Powder Ingredients. In this ratio, the formula breakdown for the preferred antimicrobial pumicing compound translates to be:

| Ingredient: | Percentage: |
| --- | --- |
| 1. Water | 48.800 |
| 2. Propylene Glycol | 2.080 |
| 3. Sodium Silicate Solution (N) | 1.040 |
| 4. Dowicil ® 200 | 0.040 |
| 5. Tetrasodium EDTA | 0.040 |
| 6. Pumice | 38.813 |
| 7. Bentonite | 7.685 |
| 8. Triclosan | 1.003 |
| 9. Triclocarban | 0.502 |
| TOTALS: | 100.00% |

The above mentioned formula was subjected to extensive in vitro testing for antimicrobial activity, proving biocidal activity repeatedly by reducing inoculum challenges of *Staphylococcus aureus* and *Klebsiella pneumoniae* by greater than 99.98% with no cidal activity on a corresponding control formulation without the antimicrobial agents.

EXAMPLE 2

The general procedure of Example 1 is repeated except that the Triclocarban is eliminated from the formulation, and the amount of pumice is increased by a corresponding percentage. The liquid phase and the powder or solid phase are combined as before in a ratio of 50% of each component. The resulting antimicrobial polishing compound was evaluated as before and found to provide excellent polishing and antimicrobial activity as well as excellent long term storage stability.

The formula breakdown for the solid or powder phase of the antimicrobial compound is:

| Ingredient: | Percentage: |
| --- | --- |
| 1. Pumice | 81.905% |
| 2. Bentonite | 16.055% |
| 3. Triclosan | 2.090% |
| TOTALS: | 100.00% |

This composition was also subjected to extensive in vitro testing, proving biocidal activity identical to the composition of Example 1 over a two (2) year period.

We claim:

1. An antimicrobial polishing compound consisting essentially of a colloidal suspension of at least about 45% by weight of each of
   (a) a liquid phase comprising, by weight of the liquid phase, about from 90 to 99% water; about from 0.5 to 10% hygroscopic solvent; about from 0.5 to 4% deflocculation agent; and up to about 0.1% each of preservative and chelating agent; and
   (b) a solid phase comprising, by weight of the solid phase, about from 70 to 90% abrasive; about from 10 to 20% colloidal suspension agent; and about from 0.5 to 2.5% of at least one antimicrobial agent.

2. An antimicrobial polishing compound of claim 1 wherein the liquid phase comprises about from 3 to 6% hygroscopic solvent.

3. An antimicrobial polishing compound of claim 2 wherein the hygroscopic solvent consists essentially of propylene glycol.

4. An antimicrobial polishing compound of claim 3 wherein the propylene glycol comprises about 4% of the liquid phase.

5. An antimicrobial polishing compound of claim 1 wherein the deflocculation agent comprises about 2% of the liquid phase and consists essentially of at least one sodium silicate composition.

6. An antimicrobial polishing compound of claim 5 wherein the preservative consists essentially of cis-1-(3-chloroallyl)-3,5,7-triaza-1-azonia adamantane chloride.

7. An antimicrobial polishing compound of claim 6 wherein the preservative is present in an amount of about from 0.05 to 0.1% of the liquid phase.

8. An antimicrobial polishing compound of claim 1 wherein the chelating agent is selected from the group consisting of sodium and calcium salts of EDTA.

9. An antimicrobial polishing compound of claim 8 wherein the chelating agent is present in an amount of about from 0.05 to 0.1% of the liquid phase.

10. An antimicrobial polishing compound of claim 8 wherein the chelating agent consists essentially of tetrasodium ethylenediamine tetracetate.

11. An antimicrobial polishing compound of claim 1 wherein the abrasive consists essentially of pumice.

12. An antimicrobial polishing compound of claim 11 wherein the solid phase comprises about from 75 to 85% pumice.

13. An antimicrobial polishing compound of claim 1 wherein the colloidal suspension agent consists essentially of bentonite.

14. An antimicrobial polishing compound of claim 13 wherein the bentonite comprises about from 14 to 18% of the solid phase.

15. An antimicrobial polishing compound of claim 1 wherein the antimicrobial agent comprises 2,4,4-trichloro-2 hydroxydiphenyl ether.

16. An antimicrobial polishing compound of claim 15 wherein the antimicrobial agent comprises about 2% of the solid phase.

17. An antimicrobial polishing compound of claim 15 wherein the antimicrobial agent further comprises 3,4,4'-trichlorocarbanilide, N-(4-chlorophenyl-N-3,4-dichlorophenyl urea.

18. An antimicrobial polishing compound of claim 17 wherein the 3,4,4'-trichlorocarbanilide, N-(4-chlorophenyl-N-3,4-dichlorophenyl urea comprises about 1% by weight of the solid phase.

19. An antimicrobial polishing compound of claim 1 wherein the liquid and solid phases are each present in an amount of at least about 48%.

20. An antimicrobial polishing compound of claim 1 wherein the liquid phase comprises about 52% and the solid phase comprises about 48%.

21. An antimicrobial polishing compound of claim 19 wherein the liquid phase and the solid phase each comprises about 50%.

* * * * *